United States Patent [19]

Raspanti et al.

[11] Patent Number: 4,530,950
[45] Date of Patent: Jul. 23, 1985

[54] PIPERIDINE DERIVATIVES AND USE THEREOF AS STABILIZERS FOR POLYMERS

[75] Inventors: Guiseppe Raspanti; Norberto Fossati; Attilio Ferrari, all of Milan, Italy

[73] Assignee: APITAL Produzioni Industriali S.p.A., Milan, Italy

[21] Appl. No.: 460,162

[22] Filed: Jan. 24, 1983

[30] Foreign Application Priority Data

Feb. 10, 1982 [IT] Italy .................. 19554 A/82

[51] Int. Cl.$^3$ .............................................. C08K 5/34
[52] U.S. Cl. .................................. 524/100; 544/207; 544/212; 544/219
[58] Field of Search ............... 524/100; 544/207, 212, 544/219

[56] References Cited

U.S. PATENT DOCUMENTS

| | | | |
|---|---|---|---|
| 3,925,376 | 12/1975 | Chalmers et al. | 524/100 |
| 4,140,673 | 2/1979 | Lachmann et al. | 524/102 |
| 4,161,592 | 7/1979 | Evans et al. | 524/100 |
| 4,191,683 | 3/1980 | Brunetti et al. | 524/100 |
| 4,321,374 | 3/1982 | Morimura et al. | 524/100 |

Primary Examiner—John Kight
Assistant Examiner—Garnette D. Draper
Attorney, Agent, or Firm—Walter H. Schneider

[57] ABSTRACT

The invention relates to novel polyalkyl piperidine derivatives and use thereof as stabilizers for polymers.

More particularly the invention relates to compounds having the general formula I

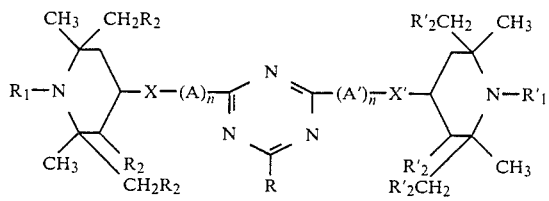

where R denotes hydrogen, alkyl, cycloalkyl, alkenyl, aralkyl or aryl;
$R_1$ and $R'_1$ denote hydrogen, alkyl, alkenyl or aralkyl;
$R_2$ and $R'_2$ denote hydrogen or methyl;
X and X' denote oxygen or $NR_3$;
$R_3$ denotes hydrogen, alkyl, cycloalkyl or aralkyl;
A and A' denote $(CH_2)_mX''$;
m equals 2 or 3;
X'' has the same meaning as X and X', and n can be 0 or 1.

11 Claims, No Drawings

PIPERIDINE DERIVATIVES AND USE THEREOF AS STABILIZERS FOR POLYMERS

DESCRIPTION OF THE INVENTION

The invention relates to novel polyalkyl piperidine derivatives and use thereof as stabilizing agents for polymers.

As is known, synthetic polymers may deteriorate through the action of heat, light or oxygen, which cause degradation, embrittlement,f discoloration and other undesirable effects.

Various classes of chemical compounds have been proposed for stabilizing polymer materials, mainly against UV radiation from sunlight. Examples of such compounds are benzophenones, benzotriazoles, α-cyanoacrylates and polyalkyl piperidine derivatives.

German Offenlegungsschrift No. 2 319 816 describes stabilizers in the form of polyalkyl piperidine derivatives having the following general formula:

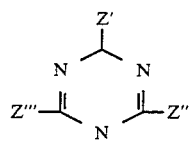

in which the three substituents Z', Z", Z''' (at least one of which contains a polyalkyl piperidine radical) are bonded to the carbon atoms of the triazine ring by a sulphur or oxygen or nitrogen atom.

It has now been found that the novel compounds having the general formula I

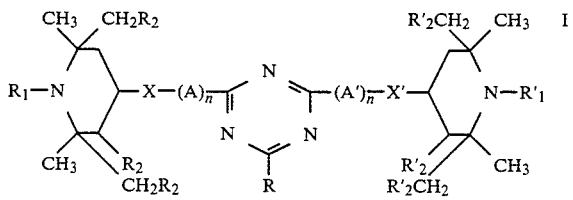

in which R denotes hydrogen, a straight-chain or branched-chain alkyl radical having 1 to 18 carbon atoms, a cycloalkyl radical having 5 to 12 carbon atoms, an alkenyl radical having 3 to 18 carbon atoms, an aralkyl radical having 7 to 9 carbon atoms or an aryl radical having 6 to 12 carbon atoms;

$R_1$ and $R'_1$ can be the same or different and denote hydrogen, a straight-chain or branched alkyl radical having 1 to 12 carbon atoms, an alkenyl radical having 3 to 8 carbon atoms, or an aralkyl radical having 7 to 19 carbon atoms;

$R_2$ and $R'_2$ can be the same or different and denote hydrogen or methyl;

X and X' can be the same or different and denote oxygen or the group N-$R_3$ in which $R_3$ denotes hydrogen, straight-chain or branched alkyl having 1 to 12 carbon atoms and containing hydroxyl groups if required, a cycloalkyl radical having 5 to 12 carbon atoms or an aralkyl radical having 7 to 12 carbon atoms, A and A' can be the same or different and denote the radical $(CH_2)m-X''$ in which $X''$ has the meaning previously defined for X and X', m can be 2 or 3 and n is equal to zero or 1; give polymer materials high stability against oxidation, particularly degradation when exposed to light.

Furthermore, products according to the invention, in contrast to commercial products, have surprisingly high resistance to the hydrolyzing effect of common detergents used in the washing of fabrics. This property is particularly useful when stabilizers are used in polyolefins or other polymers used in the production of fibres.

The following are examples of R: methyl, ethyl, propyl, isopropyl, butyl, isobutyl, pentyl, octyl, dodecyl, tetradecyl, octadecyl, allyl, butenyl, methylally, undecenyl, cyclopentyl, cyclohexyl, cyclooctyl, cyclododecyl, benzyl, methylbenzyl, dedecylbenzyl, phenyl and diphenylyl.

The following are examples of $R_1$ and $R'_1$: hydrogen, methyl, ethyl, propyl, butyl, hexyl, octyl, dodecyl, allyl, butenyl and benzyl.

The invention also relates to salts of the formula-I compound with inorganic acids, e.g. chlorides, sulphates and phosphates, or with organic acids, e.g. acetates, citrates, tartrates, maleates, stereates, oxalates or benzoates.

A preferred sub-group of compounds according to the invention are those corresponding to formula Ia:

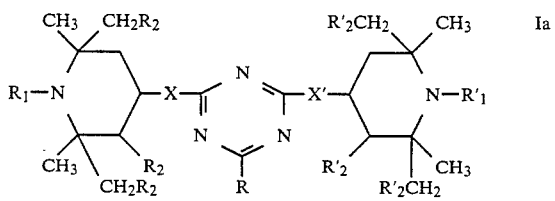

in which R, $R_1$, $R'_1$, $R_2$, $R'_2$, X and X' have the meanings previously defined for formula I.

The invention also relates to the use of compounds having the general formula I as stabilizers for polymers.

Formula-I compounds are excellent stabilizers which give polymer materials, particularly polyolefins, very high stability against degradation caused by heat, oxygen or more particularly ultraviolet radiation from sunlight.

According to the invention, "polymers" denote polyethylenes, polypropylenes, polystyrenes, polybutadienes, polyisoprenes and copolymers thereof, polyvinyl chloride, polyvinylidene chloride and copolymers thereof, polyvinyl acetate and copolymers thereof, more particularly with ethylene, polyesters such as polyethylene terephthalate, polyamides such as Nylon 6 and Nylon 6,6 and polyurethanes.

Compounds I can be incorporated in polymers by any known method of mixing additives with polymer materials. For example, formula I compounds can be mixed with the polymer in a suitable mixer, or can be added in solution or suspension form in a suitable solvent such as methanol or ethanol or acetone, the solvent being removed after intimately mixing with the polymer, which can be in the form of a powder, granulate or suspension. Alternatively, formula I compounds can be added to the polymer during the preparation thereof, e.g. in the last stage of preparation.

Formula I compounds can also be added together with other kinds of commonly-used stabilizers and additives, e.g. anti-oxidizing agents based on phenols, amines, phosphites, UV absorbers based on benzotriazoles and benzophenones, plasticizing agents, lubricants, antistatic agents, anti-flame agents or titanium oxide. The amount of formula I compounds required for efficient stabilization of the polymer depends on various factors, such as the type and characteristics of the polymer, the use for which it is intended, the intensity of radiation and the duration of exposure. Usually a quantity of 0.01 to 5% by weight of the polymer, preferably 0.1 to 1.0%, is sufficient.

The invention also relates to a method of preparing compounds having the general formula I by reacting a substituted triazine having the formula II

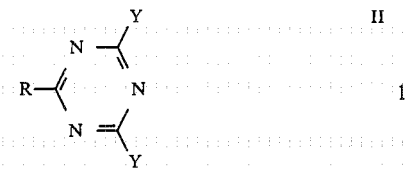

in which R has the meaning defined previously and Y denotes bromine or chlorine, preferably chlorine, with a compound having the formula III

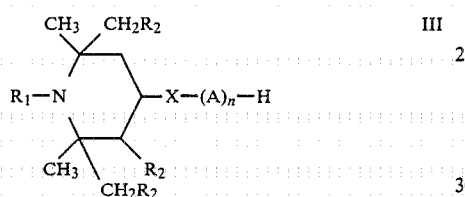

in which $R_1$, $R_2$, X, (A) and n have the previously-defined meanings.

Compounds having the formula II or III are known and can be prepared by known methods.

In the reaction, two or more mols of formula III compound are used per mol of formula II compound. Solvents such as toluene, xylene, acetone, dimethyl formamide or other aprotic solvents can be used for the reaction. Preferably the reaction is performed in the presence of acid acceptors such as organic or inorganic bases, e.g. triethylamine, pyridine, sodium or potassium hydroxide, or sodium or potassium carbonate or bicarbonate.

In order to synthesise formula I compounds in which X (or X′ or X″ respectively) denotes oxygen, it is preferable first to prepare an alkoxide from the formula III intermediate by reacting it with metallic potassium or sodium.

In order to prepare formula I compounds which are asymmetrical, i.e. where the two piperidine groups are different from one another, synthesis can be carried out in a number of stages, by first reacting 1 mol of substituted formula II halogen triazine with 1 mol of formula III compound to obtain compounds having the formula IV:

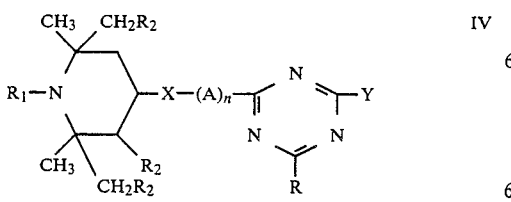

where R, $R_1$, $R_2$, X, A, n and Y have the previously-defined meanings, and subsequently reacting the formula IV compound with 1 mol of a formula III compound with various values for $R_1$, $R_2$, X, A and/or n, to obtain compounds having the formula I.

The desired products are isolated from the reaction mixture and purified by conventional methods.

The following is a list of representative but non-limitative examples of formula I compounds:

2-octyl-4,6-bis-[(2′,2′,6′,6′-tetramethyl-piperidine-4′-yl)-amino]-1,3,5-triazine 2-dodecyl-4,6-bis-[(2′,2′,6′,6′-tetramethyl-piperidine-4′-yl)-amino]-1,3,5,-triazine 2-cyclohexyl-4,6-bis-[(2′,2′,6′,6′-tetramethyl-piperidine-4′-yl)-amino]-1,3,5-triazine 2-butyl-4,6-bis-[(2′,2′,6′,6′-tetramethyl-piperidine-4′-yl)-ethyl amino]-1,3,5-triazine 2-dodecyl-4,6-bis-[2′,2′,6′,6′-tetramethyl-piperidine-4′-yl)-ethyl amino]-1,3,5-triazine 2-butyl-4,6-bis-[(2′,2′,6′,6′-tetramethyl-piperidine-4′-yl)-ethyl amino]-1,3,5-triazine 2-ethyl-4,6-bis-[(2′,2′,6′,6′-tetramethyl-piperidine-4′-yl)butylamino]-1,3,5-triazine 2butyl-4,6-bis-[(2′,2′,6′,6′-tetramethyl-piperidine-4′-yl)butylamino]-1,3,5-triazine 2-octyl-4,6-bis-[(2′,2′,6′,6′-tetramethyl-piperidine-4′-yl)-butylamino]-1,3,5-triazine 2-phenyl-4,6-bis-[(2′,2′,6′,6′-tetramethyl-piperidine-4′-yl)-butylamino]-1,3,5-triazine 2-octyl-4,6-bis-[(1′,2′,2′,6′,6′-pentamethyl-piperidine-4′-yl)-amino]-1,3,5-triazine 2-cyclohexyl-4,6-bis-[(1′,2′,2′,6′,6′-pentamethyl-piperidine-4′-yl)-ethylamino]-1,3,5-triazine 2-butyl-4,6-bis-[(1′,2′,2′,6′,6′-pentamethyl-piperidine-4′-yl)-butylamino]-1,3,5-triazine 2-octyl-4,6-bis-[(2′,2′,6′,6′-tetramethyl-piperidine-4′-yl)-oxy]-1,3,5-triazine 2-dodecyl-4,6-bis-[(2′,2′,6′,6′-tetramethyl-piperidine-4′-yl)-oxy]-1,3,5-triazine 2-benzyl-4,6-bis-[(2′,2′,6′,6′-tetramethyl-piperidine-4′-yl)-oxy]-1,3,5-triazine 2-phenyl-4,6-bis-[(1′,2′,2′,6′,6′-pentamethyl-piperidine-4′-yl)-oxy]-1,3,5-triazine 2-octyl-4,6-bis-[(1′-allyl-2′,2′,6′,6′-tetramethyl-piperidine-4′-yl)-oxy]-1,3,5-triazine 2-butyl-4,6-bis-[(1′-benzyl-2′,2′,6′,6′-tetramethyl-piperidine-4′-yl)-oxy]-1,3,5-triazine 2-ethyl-4,6-bis-[(2′,2′,6′,6′-tetramethyl-piperidine-4′-yl)-2″-hydroxyethylamino]-1,3,5-triazine 2-octyl-4,6-bis-[(2′,2′,6′,6′-tetramethyl-piperidine-4′-yl)-2″-hydroxyethylamino]-1,3,5-triazine 2-butyl-4,6-bis-[(1′,2′,2′,6′,6′-pentamethyl-piperidine-3′-yl)-2″-oxyethoxy]-1,3,5-triazine 2-phenyl-4,6-bis-[(1′,2′,2′,6′,6′-pentamethyl-piperidine-4′-yl)-2″-oxyethoxy]-1,3,5-triazine 2-dodecyl-4,6-bis-[(2′,6′-diethyl-2′,3′,6′-trimethyl-piperidine-4′-yl)-amino]-1,3,5-triazine 2-butyl-4,6-bis-[(2′,6′-diethyl-2′,3′,6′-trimethyl-piperidine-4′-yl)-butylamino]-1,3,5-triazine 2-octyl-4,6-bis-[(2′,6′-diethyl-2′,3′,6′-trimethyl-piperidine-4′-yl)-oxy]-1,3,5-triazine 2-butyl-4-[(2′,2′,6′,6′-tetramethyl-piperidine-4′-yl)-butylamino]-6-[(2″,2″,6″,6″-tetramethyl-piperidine-4″-yl)-oxy]-1,3,5-triazine 2-octyl-4-[(2′,2′,6′,6′-tetramethyl-piperidine-4′-yl)-butylamino]-6-[(2″,2″,6″,6″-tetramethyl-piperidine-4″-yl)-amino]-1,3,5-triazine 2-benzyl-4-[(2',2',6',6'-tetramethyl-piperidine-4'-yl)-amino]-6-[(1",2",2",6",6"-pentamethyl-piperidine-4"-yl)-2-oxyethoxy]-1,3,5-triazine
2-(2",4"-dimethyl phenyl)-4,6-bis[(2',2',6',6'-tetramethyl-piperidine-4'-yl)-oxy]-1,3,5-triazine

EXAMPLES 1–5

12.2 g of 4-butyl amino-2,2,6,6 tetramethyl piperidine followed by 2.6 g NaOH dissolved in 6 ml water were added to 6 g of 2-butyl-4,6-dichloro-1,3,5-triazine suspended in 250 ml of water.

The mixture was stirred for 30 minutes at ambient temperature, then reflux-heated and stirred for 10 hours.

It was cooled and 200 ml ethyl ether was added. After the phases had been separated, the organic phase was washed with water and dried and the solvent was evaporated.

The residue was recrystallized from acetonitrile, giving the hydrate of 2-butyl-4,6-bis-[(2',2',6',6'-tetramethy-piperidine-4-yl-butylamino)]-1,3,5-triazine, in the form of a white substance melting at 71°/74° C.

Analysis (anhydrous compound): Found (C: 70.91; H: 11.24; N: 16,87; Calculated C: 71.00; H: 11.31; N:17.59.

The compounds in Table 1 were prepared by operating in the same manner.

TABLE 1

| EXAMPLE | R | M.P. °C. | EMPIRICAL FORMULA | ANALYSIS (ANHYDROUS) | | |
|---|---|---|---|---|---|---|
| 2 | n-$C_8H_{17}$ | 68–69 | $C_{37}H_{71}N_7 \cdot XH_2O$ | Found C: 72,25 | H: 11,85 | N: 15,55 |
|   |   |   |   | Calc. C: 72,43 | H: 11,58 | N: 15,99 |
| 3 | n-$C_{12}H_{25}$ | 70–71 | $C_{41}H_{79}N_7 \cdot XH_2O$ | Found C: 72,94 | H: 12,15 | N: 14,35 |
|   |   |   |   | Calc. C: 73,54 | H: 11,81 | N: 14,65 |
| 4 | ⟨Ph⟩–$CH_2$– | 82–86 | $C_{36}H_{61}N_7 \cdot XH_2O$ | Found C: 72,68 | H: 10,86 | N: 16,31 |
|   |   |   |   | Calc. C: 73,10 | H: 10,32 | N: 16,58 |
| 5 | ⟨Ph⟩– | 132–134 | $C_{35}H_{59}N_7$ | Found C: 72,90 | H: 10,24 | N: 16,97 |
|   |   |   |   | Calc. C: 72,79 | H: 10,23 | N: 16,98 |

EXAMPLES 6–10

2.4 g sodium was added to 15.7 g 4-hydroxy-2,2,6,6-tetramethyl piperidine in 120 ml xylene.

The mixture was reflux-heated for 12 hours and then cooled to 25° C., the unreacted sodium was removed and 13.4 g 2-dodecyl-4,6-dichloro-1,3,5-triazine dissolved in 30 ml xylene was added.

The reaction mixture was reflux-heated and stirred for 2 hours, after which the solvent was removed and the residue was dissolved in 200 ml water at 60° C. The solid which formed was filtered, washed, dried and recrystallized from acetonitrile, giving 2-dodecyl-4,6-bis-[(2',2',6',6'-tetramethyl piperidinyl-4-oxy)]-1,3,5-triazine in the form of a white substance melting at 78°–71° C.

Analysis: Found C: 70.80; H: 11.21; N: 12.30; Calc. C: 70.84; H: 10.91; N: 12.53.

The compounds in Table II were prepared by operating in the same manner.

TABLE 2

| EXAMPLE | R | M.P. °C. | EMPIRICAL FORMULA | ANALYSIS | | |
|---|---|---|---|---|---|---|
| 7 | n-$C_4H_9$ | 93–95 | $C_{25}H_{45}N_5O_2$ | Found C: 66,76 | H: 10,51 | N: 15,90 |
|   |   |   |   | Calc. C: 67,11 | H: 10,07 | N: 15,66 |
| 8 | n-$C_8H_{17}$ | 68–69 | $C_{29}H_{53}N_5O_2$ | Found C: 69,15 | H: 10,60 | N: 13,80 |
|   |   |   |   | Calc. C: 69,19 | H: 10,54 | N: 13,92 |
| 9 | ⟨Ph⟩– | 171–172 | $C_{27}H_{41}N_5O_2$ | Found C: 69,55 | H: 8,94 | N: 14,90 |
|   |   |   |   | Calc. C: 69,38 | H: 8,78 | N: 14,99 |

TABLE 2-continued

[Chemical structure: A triazine ring with two O-linked 2,2,6,6-tetramethylpiperidin-4-yl groups bearing NH, and an R substituent on the triazine]

| EXAMPLE | R | M.P. °C. | EMPIRICAL FORMULA | ANALYSIS | | | |
|---|---|---|---|---|---|---|---|
| 10 | [2,4-dimethylphenyl: CH$_3$–C$_6$H$_3$(CH$_3$)–] | 179–181 | C$_{29}$H$_{45}$N$_5$O$_2$ | Found<br>Calc. | C: 70,1<br>C: 70,3 | H: 9,15<br>H: 9,09 | N: 13,95<br>N: 14,14 |

EXAMPLE 11

9.4 g of 4-amino-2,2,6,6-tetramethyl-piperidine and 2.3 g of NaOH dissolved in 20 ml water were added to 6.2 g of 2-butyl-4,6-dichloro-1,3,5-triazine in 170 ml water. The mixture was stirred for 30 minutes at ambient temperature, then reflux-heated and stirred for 12 hours.

The mixture was cooled and the solid which formed was filtered, washed, dried and crystallized from dioxane, giving 2-butyl-4,6-[(2′,2′,6′,6′-tetramethylpiperidine-4-yl-amino)]-1,3,5-triazine melting at 182°–183° C.

Analysis Found C: 67.30; H: 10.90; N: 21.77; Calculated C: 67.41; H: 10.56; N: 22.02.

EXAMPLE 12

300 grams polypropylene (Moplen F 020 produced by Messrs. Montedison), 0.6 g calcium stearate and 0.6 g n-octadecyl-3-(3,5-di-tert-butyl-4-hydroxyphenyl)-proprionate were mixed with 0.75 g of a stabilizer from Table 3 dissolved in 30 ml acetone. The solvent was then removed in vacuo at 50° C.

The dry mixture was then additionally mixed and homogenized in a mixer at a temperature of 200° C. for 10 minutes. The resulting composition was converted, by pressure at 260° C., into films 0.2 mm thick. Samples were cut from these films and irradiated with UV light in a Xenotest 150. The irradiated samples were periodically examined in infrared light, determining the increase with time in the carbonyl band at 5.85μ compared with a sample not containing compounds from Table 1 and 2. The time (T 0.1) necessary for obtaining an increase of 0.1 in the extinction of carbonyl was determined.

The results are illustrated in Table 3

TABLE 3

| Stabilizer | T 0.1 (hours) |
|---|---|
| Without stabilizer | 300 |
| Compound from Example 1 | >1000 |
| Compound from Example 2 | >1000 |
| Compound from Example 3 | >1000 |
| Compound from Example 5 | >1000 |
| Compound from Example 6 | >1000 |
| Compound from Example 8 | >1000 |

EXAMPLE 13

300 grams of high-density polyethylene (Moplen RO produced by Messrs. Montedison), 0.9 g of n-octadecyl-3-(3,5-tert.butyl-4-hydroxy-phenyl)-propionate and 0.3 g calcium stearate were mixed with 0.6 of a stabilizer from Table 4, dissolved in 30 ml acetone.

After the solvent had been removed in vacuo at 50° C., the dry mixture was additionally mixed and homogenized at 190° C. in a mixer. The resulting composition was converted, by pressure at 200° C., into films as described in Example 11, the time necessary to obtain an increase of 0.05 in the extinction of carbonyl being determined. The results are illustrated in Table 4.

TABLE 4

| Stabilizer | T 0.05 (hours) |
|---|---|
| Without stabilizer | 350 |
| Compound from Example 1 | >1500 |
| Compound from Example 2 | >1500 |
| Compound from Example 4 | >1500 |
| Compound from Example 6 | >1500 |
| Compound from Example 7 | >1500 |
| Compound from Example 8 | >1500 |

EXAMPLE 14

300 grams of polypropylene (Moplen F 020 produced by Messrs. Montedison), 0.6 g calcium stearate and 0.6 g of n-octadecyl-J-(3,5-ditert.-butyl-4-hydroxyphenyl)-propionate were mixed with 0.75 g of a stabilizer belonging to the following group:

A compound from Example 9
Tinuvin 770 and
A compound from Example 1 of DOS 2319816.

Stabilizers in the form of a solution in 30 ml acetone were added to the mixture.

The solvent was then removed in vacuo at 50° C. The dry mixture was then additionally homogenized in a mixer at a temperature of 200° C. for 10 minutes. The resulting composition was converted by pressure at 260° C. into films 0.2 mm thick.

Samples were cut from the films and irradiated with UV light in a Xenotest 150.

The irradiated samples were periodically examined in infrared light to determine the increase with time in the carbonyl band at 5.85, the time (T 0.1) necessary to obtain an increase of 0.1 in carbonyl extinction being determined. The extinction was measured every 100 hours after 1000 hours.

The results are illustrated in Table 5.

TABLE 5

| Stabilizer | T 0.1 (hours) |
|---|---|
| Compound from Example 9 | 2500 |
| Tinuvin 770 | 2500 |
| Compound as in the Example in DOS 2319816 | 1800 |

EXAMPLE 15

0.5 grams of a product from Example 9 and Tinuvin 770 were suspended, in separate tests, in 100 ml water containing 5 g of detergents (Dixan) in solution. The mixture was heated to 90° C. and kept at the same temperature for a number of hours, the percentage of hydrolyzed product being periodically determined. The results are summarized in the following Table:

| Hours | % hydrolysis produced in Example 9 | % hydrolysis in Tinuvin 770 |
|---|---|---|
| 5 | Practically none | 6.5% |
| 10 | " | 13.8% |
| 15 | " | 18% |
| 20 | " | 23% |

We claim:

1. Compounds having the general formula I

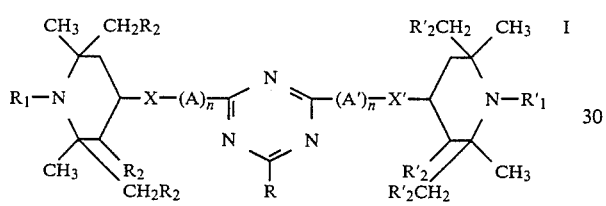

in which R denotes hydrogen, a straight-chain or branched-chain alkyl radical having 1 to 18 carbon atoms, a cycloalkyl radical having 5 to 12 carbon atoms, an alkenyl radical having 3 to 18 carbon atoms, an aralkyl radical having 7 to 19 carbon atoms or an aryl radical having 6 to 12 carbon atoms;

$R_1$ and $R'_1$ can be the same or different and denote hydrogen, a straight-chain or branched alkyl radical having 1 to 12 carbon atoms, an alkenyl radical having 3 to 8 carbon atoms, or an aralkyl radical having 7 to 19 carbon atoms;

$R_2$ and $R'_2$ can be the same or different and denote hydrogen or methyl;

X and X' can be the same or different and denote oxygen or the group $N-R_3$ in which $R_3$ denotes hydrogen, a straight-chain or branched alkyl or hydroxyalkyl radical having 1 to 12 carbon atoms, a cycloalkyl radical having 5 to 12 carbon atoms, or an aralkyl radical having 7 to 12 carbon atoms, A and A' can be the same or different and denote the radical $(CH_2)_m-X''$ in which $X''$ has the meaning previously defined for X and X', and is a direct bond to the triazine ring, m can be 2 or 3 and n is equal to zero or 1, and salts thereof with organic or inorganic acids.

2. Compounds according to claim 1 having the formula:

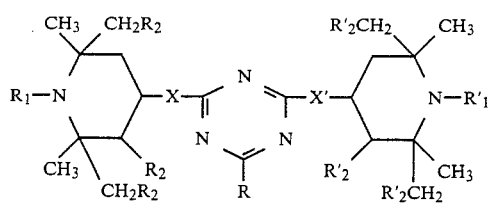

where R, $R_1$, $R'_1$, $R_2$, $R'_2$, X and X' have the meanings defined in claim 1.

3. Compounds according to claim 1 having the formula:

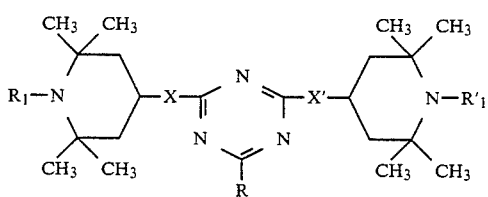

where R, $R_1$, $R'_1$, X and X' have the meanings defined in claim 1.

4. Compounds according to claim 1 having the formula:

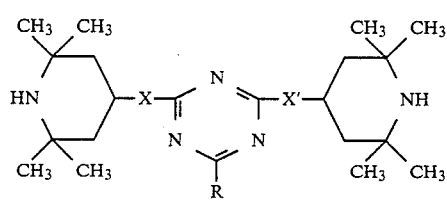

wherein R, X and X' have the meanings defined in claim 1.

5. Compounds according to claim 1 having the formula:

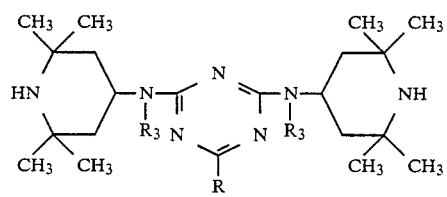

where R and $R_3$ have the meanings defined in claim 1.

6. Compounds according to claim 1 having the formula:

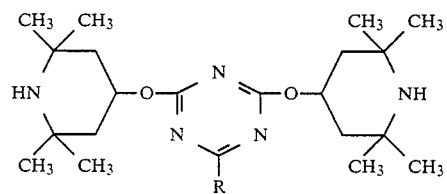

7. Compounds according to claim 1 having the formula:

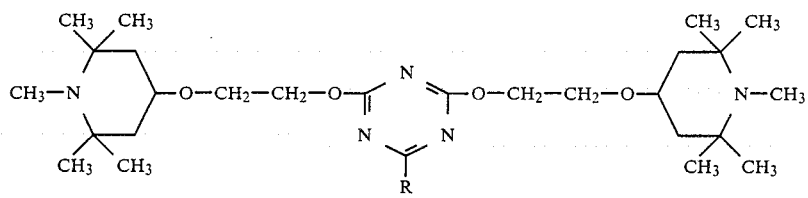

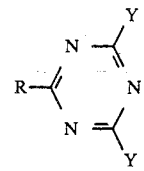

where R has the meaning defined in claim 1.

8. Compounds according to claim 1 having the formula:

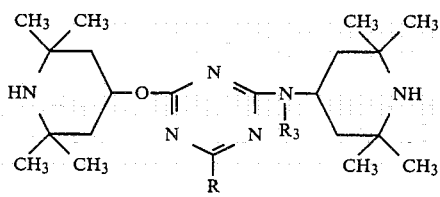

where R and $R_3$ have the meanings defined in claim 1.

9. A method of preparing compounds having the formula I according to claim 1, characterized in that one mol of a substituted triazine having the formula II where R has the meaning defined in claim 1 and Y denotes chlorine or bromine, is reacted with 2 or more mols of a compound having the formula III

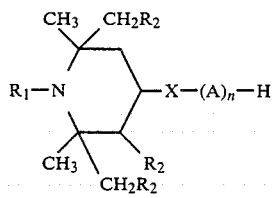

where R, $R_1$, $R_2$, X, (A) and n have the meanings previously defined.

10. A method of stabilizing a polymer against the deteriorating effects of ultra-violet radiation which comprises incorporating in the polymer 0.1–5.0% by weight of the polymer of a compound according to claim 1.

11. A polymer composition stabilized against the deteriorating effects of ultra-violet radiation comprising a polymer and 0.0–5.0% by weight of the polymer of a compound according to claim 1.

* * * * *